United States Patent [19]

Hood

[11] Patent Number: 5,371,305
[45] Date of Patent: Dec. 6, 1994

[54] PROCESS FOR PRODUCING PHENOL FROM CUMENE

[75] Inventor: Horace E. Hood, Wilmington, Del.

[73] Assignee: Hercules Incorporated, Wilmington, Del.

[21] Appl. No.: 998,985

[22] Filed: Dec. 31, 1992

[51] Int. Cl.$^5$ .................... C07C 37/08; C07C 15/00
[52] U.S. Cl. .................... 568/798; 568/385; 568/741; 568/754; 568/768; 585/405; 585/435
[58] Field of Search ............ 568/385, 741, 754, 768, 568/798, 485; 585/405, 435

[56] References Cited

U.S. PATENT DOCUMENTS

| | | | |
|---|---|---|---|
| 4,016,213 | 4/1977 | Yeh et al. | 568/798 |
| 4,173,587 | 11/1979 | Wu et al. | 568/798 |
| 4,207,264 | 6/1980 | Anderson et al. | 568/798 |
| 4,310,712 | 1/1982 | Langley | 568/798 |
| 4,358,618 | 11/1982 | Sifniades et al. | 568/798 |
| 4,929,786 | 5/1990 | Himmele et al. | 585/435 |
| 5,015,786 | 5/1991 | Araki et al. | 568/798 |
| 5,017,729 | 5/1991 | Fukuhara et al. | 568/798 |
| 5,144,094 | 9/1992 | Richmond et al. | 568/635 |
| 5,254,751 | 10/1993 | Zakoshansky | 568/798 |

FOREIGN PATENT DOCUMENTS 0080332  5/1982  Japan ................... 585/435

OTHER PUBLICATIONS

Beltrame, Pier Luigi, et al. (University of Milan, Italy), "Side Reactions in the Phenol/Acetone Process. A Kinetic Study", Ind. Eng. Chem. Res. 1988, 27, pp. 4–7.

Primary Examiner—Werren B. Lone
Attorney, Agent, or Firm—Mark Goldberg

[57] ABSTRACT

The present invention provides in a particular embodiment an improvement in the process for producing phenol by the acid-catalyzed cleavage of cumene hydroperoxide (CHP). The reactant stream fed to the cleavage reactor also includes the contaminant by-product dimethyl benzyl alcohol (DMBA) formed during the direct oxidation of cumene to CHP. This contaminant DMBA further reacts in the cleavage reactor to reduce the yield of phenol and produce undesirable and unreclaimable by-products. The improvement provided herein comprises performing the cleavage reaction at a reduced residence time of generally from one-half to five minutes, whereby the formation of α-methyl styrene from DMBA is promoted and the formation of the undesirable and unreclaimable by-products is reduced; α-methyl styrene is not only a useful by-product, but can be recycled and hydrogenated to the cumene starting material.

17 Claims, 14 Drawing Sheets

CHP

(1) $\quad F(CHP) = F(CHP)_0 - k_1 (CHP) V$ $\quad\quad$ OUT $=$ IN $-$ REACTED $\quad\quad \tau = V/F$ (1.1) $\quad (CHP) = (CHP)_0 - k_1 \tau (CHP)$

DMBA

(2) $\quad (DMBA) = (DMBA)_0 - k_2 \tau (DMBA)$ (2.1) $\quad (DMBA)_0 = (DMBA) + (AMS) + (CP) + 2(AMSD)$ $\quad\quad$ CP + CUMYLPHENOL $\quad\quad$ AMSD = AMS Dimer Phenol (3)  $F(PH) = k_1(CHP)V - k_3(PH)(AMS)V$ $PH = \text{Phenol}$ (3.1)  $(PH) = k_1(CHP)\tau - k_3(PH)(AMS)\tau$

AMS (4)  $F(AMS) = k_2(DMBA)V - k_3(PH)(AMS)V - k_4(AMS)^2 V$ (4.1)  $(AMS) = k_2(DMBA)\tau - k_3(PH)(AMS)\tau - k_4(AMS)^2\tau$

CUMYLPHENOL (5)  $F(CP) = k_3(PH)(AMS)V$ (5.1)  $(CP) = k_3(PH)(AMS)\tau$

AMS DIMER (6)  $F(AMSD) = k_4(AMS)^2 V$ (6.1)  $(AMSD) = k_4(AMS)^2 \tau$

FIG.2b

PROCESS FOR PRODUCING PHENOL FROM CUMENE

BACKGROUND OF THE INVENTION

1. The Field of the Invention

The present invention relates to improvements in the process of producing aryl alcohols from aralkyl hydroperoxides, especially to the production phenol from cumene, and most particularly to improving the yields of phenol and reclaimable by-products such as α-methylstyrene.

2. The State of the Art

Phenol, also known as carbolic acid, is a fundamental starting material for the production of a wide range of organic chemicals. Particularly important are the use of phenol for the manufacture of phenol-formaldehyde resins, and for making bisphenol-A (2,2-bis(4-hydroxyphenyl)propane), which is used in the manufacture of polycarbonate resins (e.g., Lexan TM). Phenol is typically produced by either the "cumene process" or the "Raschig process."

The cumene-to-phenol process generally comprises oxidizing cumene, $C_6H_5$—$CH(CH_3)_2$, in air to form cumene hydroperoxide (CHP), $C_6H_5$—$C(OOH)(CH_3)_2$. This hydroperoxide is then cleaved under dilutely acidic conditions to form the phenol product and acetone (2-propanone) as a useful by-product. Acetone and phenol can be used to produce bisphenol-A, which is condensed with phosgene to produce polycarbonate plastics.

In the first step of the cumene-to-phenol process, typically air is bubbled through cumene, at elevated temperatures, with or without the presence of aqueous sodium carbonate, to produce CHP. During this oxidation step, contaminant by-products, particularly α,α-dimethylbenzyl alcohol (DMBA; also variously called dimethyl phenyl carbinol, DMPC, or DMFC) and acetophenone (AP), are formed. This oxidation reaction is the primary generator of yield-loss by-products in the cumene-phenol process. There are additional impurities in the products of the oxidation reaction, such as unreacted cumene, and formic and carbonic acids and their salts.

In the cumene-phenol process, dilute acid is used to cleave CHP and produce phenol and acetone. The DMBA contaminant by-product present in the CHP fed to the cleavage reactor dehydrates in the dilutely acidic reaction mixture to form AMS, as just noted. However, the presence in the reaction mixture of the phenol product as well as the acetone, CHP, AP, and water by-products, plus unreacted cumene, allow for further reactions. Those of particular importance are the detrimental reactions of the phenol product with AMS to form cumylphenol and of AMS with itself to form AMS dimer because of their contribution to the yield loss, and the reaction of DMBA with CHP to form dicumyl peroxide (DCP) and water. AMS dimer and cumylphenol are essentially waste by-products from which recovery of useful products is very difficult and expensive; DCP is cleaved by the acid catalyst in the reaction mixture to produce phenol, acetone, AMS.

This cleavage reaction is applicable to aralkyl hydroperoxides in general. More importantly, this type of cleavage reaction is very rapid and very exothermic. (See, e.g., V. G. Jung and G. Just, J. prakt. Chem., 313, 377 (1971), who describe a study of the kinetics of the CHP cleavage reaction using fast flow in small tubes.)

To facilitate removing the heat generated in the cleavage reaction and thereby control the reaction, commercial plants use continuously-stirred tank reactors (CSTRs) operating with acetone reflux. The reaction medium comprises mostly the reaction products, phenol and acetone, with only minimal concentrations ($<1\%$) of CHP. The reaction mixture also contains significant amounts of the contaminant by-products and the various cleavage reaction by-products.

U.S. Pat. No. 4,358,618 teaches a variation on the cumene process whereby the formation of DCP as an intermediate is promoted in a first reaction step, and then the DCP is decomposed in a second reaction step to yield phenol, acetone, and AMS. The residence times and reaction temperatures are chosen to balance the maximization of DCP in the first step and its subsequent decomposition to phenol and AMS. It is also suggested that a third, small tubular reactor be used between the two steps to promote the decomposition of CHP remaining after the first reaction step.

U.S. Pat. No. 4,173,587 discloses the use of a rhenium-containing catalyst for high selectivity in producing phenol and acetone from the cleavage of CHP and subsequently recovering DMBA by distillation. Reaction times are between ten and 25 minutes. Also, the AMS derived in this process appears to be derived from the CHP as a by-product of the rhenium-catalyzed reaction, rather than derived from the dehydration DMBA formed during oxidation of cumene as for the general process noted above.

U.S. Pat. No. 4,016,213 varies the typical cumene process by immediately neutralizing the reaction product to prevent the dehydration of DMBA to AMS.

U.S. Pat. No. 4,207,264 is particularly concerned with the formation of highly colored by-products, of concern typically in the production of hydroquinone (1,4-para-dihydroxy benzene) from p-diisopropylbenzene dihydroperoxide; hydroquinone is used as a rubber antioxidant. To avoid these by-products, the cleavage reaction is conducted in a tubular reactor to prevent any portion of the reaction mixture from remaining in the reaction zone longer than the desired average residence time. Residence times of one to 15 min., preferably five to 12 min., are taught.

P. L. Beltrame et al., "Side Reactions in the Phenol-/Acetone Process. A Kinetic Study," Ind. Eng. Chem. Res., 27, 4–7, 1988, discuss the reaction of dimethylphenylcarbinol (DMFC) in the presence of phenol, acetone, and sulfuric acid to give AMS and other by-products, including diphenyl-substituted pentenes, cumylphenol, and phenyl cumyl ether. The kinetics are derived using a reaction scheme having a carbocation intermediate. They teach that phenol assists the acid-catalysis of various reactions and thus the total acidity of the reaction mixture (sulfuric acid plus phenol) strongly effects the reaction time leading to the maximum AMS yield.

U.S. Pat. No. 4,310,712 discloses a process of producing phenol, acetone and AMS from cumene hydroperoxide using a sulfuric acid catalyst in a reactor without significant back-mixing (i.e., with plug-flow) and controlling the reaction temperature by evaporation of acetone from the reaction mixture. In contrast, U.S.S.R. Pat. No. 851,851 discloses decomposing cumene hydroperoxide in a multisection reactor and adding cold acetone to each section to stabilize the reaction temperature. These contrasting disclosures illustrate how important the type of reactor and reaction rate can be to controlling this process.

SUMMARY OF THE INVENTION

In view of the state of the art, it would be beneficial to reduce phenol losses due to the formation of DMBA in the oxidation step of the cumene-phenol process.

It would also be beneficial to reduce phenol losses due to the formation of cumylphenol in the step of cleaving CHP.

Another object of this invention is to maximize the dehydration of DMBA to produce AMS during the cleavage reaction, and without the subsequent loss of AMS due to the formation of AMS-dimer or cumylphenol.

Still another object of this invention is to reduce the net cumene consumption by recovering and then hydrogenating AMS back to cumene for recycling to the start of the process. Alternatively, AMS can be recovered and purified for sale, thereby economically off-setting the yield loss.

In one embodiment, this invention is directed to an improvement in the process for the production of phenol or a derivative thereof by the acid-catalyzed cleavage of a feedstock comprising a reactant aralkyl hydroperoxide and a contaminant by-product aralkyl alcohol to convert the hydroperoxide to phenol (or said derivative thereof) and an alkylcarbonyl compound. The improvement provided by this invention is that the cleavage reaction occurs in at least one stirred reactor during a residence time of not more than about seven minutes; the preferred residence time is between about one and four minutes. In various embodiments, the reaction is conducted in a series of one or more reactors in which the first in the series is a continuously-stirred tank reactor and others in the series may include plug flow reactors.

BRIEF DESCRIPTION OF THE DRAWINGS

FIGS. 2A and 2B depict the cleavage reaction kinetics for the Network shown in FIG. 1.

DETAILED DESCRIPTION OF PREFERRED EMBODIMENTS

As noted previously, the cumene-to-phenol process is applicable to aralkyl hydroperoxides in general, which can be represented as $Ar-[C(OOH)R^1R^2]_x$, wherein Ar is aryl, optionally further substituted, and including polynuclear aromatic compounds, $R^1$ and $R^2$ are independently selected from among hydrogen, alkyl, and cycloalkyl groups, and x is an integer from 1 to 4. The aralkyl hydroperoxide is typically produced by the oxidation of the corresponding aralkyl compound $Ar-[CHR^1R^2]_x$. The resulting aralkyl hydroperoxide is cleaved in a catalyzed reaction, typically using dilute acid, although more expensive catalysts are also available. The products of the cleavage reaction are an aryl alcohol $Ar-[OH]_x$ and an alkyl carbonyl by-product $OCR^1R^2$; thus, phenol and acetone are produced where the starting CHP material is defined by $x=1$ and both $R^1$ and $R^2$ are methyl. While the present invention is concerned primarily with the production of phenol and the by-product acetone, this invention is applicable to the production of phenol derivatives, especially those having commercial utility, such as hydroquinone. During the oxidation reaction, aralkyl alcohols such as DMBA, as well as aromatic ketones such as AP, are produced from the aralkyl compound. The formation of these contaminant by-products due to conventional oxidation in air is inevitable.

Figure 1:
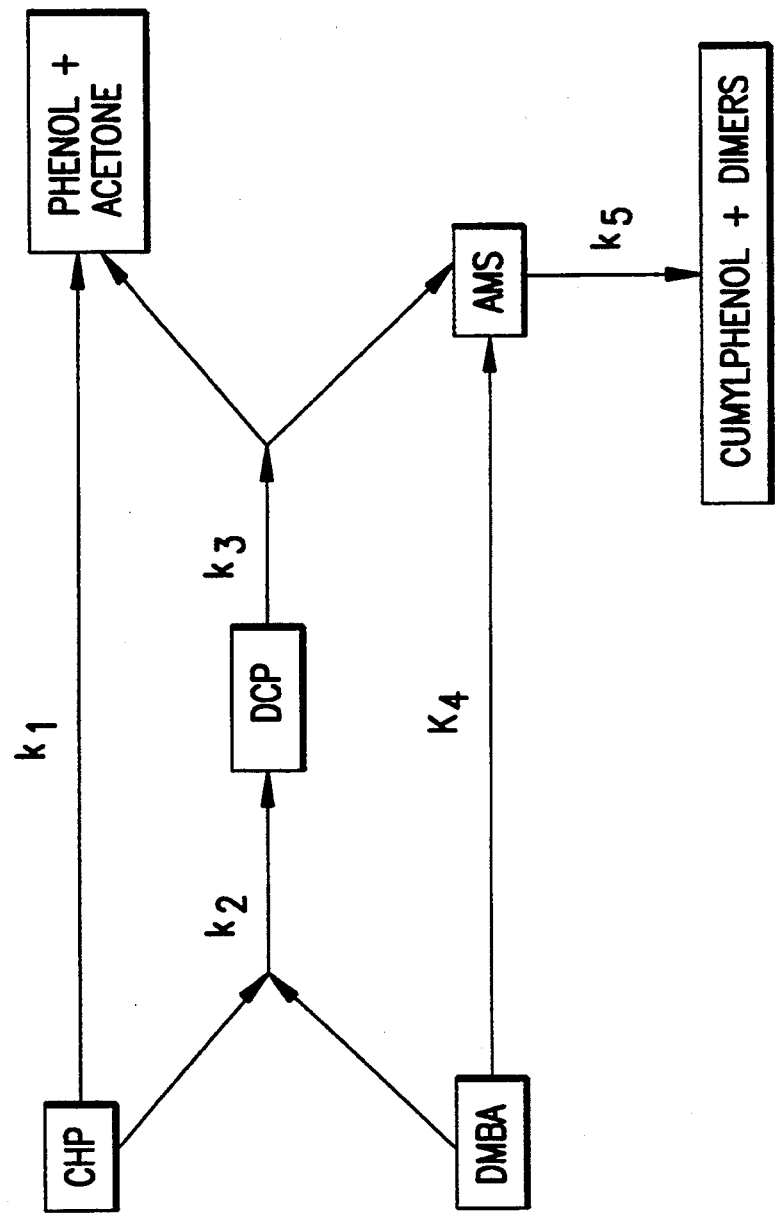
FIG. 1 depicts the CHP Cleavage Reaction Network.

During the acid-catalyzed cleavage reaction, the aralkyl alcohol DMBA is partially dehydrated to an aralkenyl compound such as AMS, which is a commercially useful product that can be recovered, isolated, and sold if economic conditions are favorable. It is known that the process yield loss of cumene to DMBA can be offset by promoting the dehydration of DMBA to AMS, and then hydrogenating the AMS to produce cumene starting material. However, one problem with reclaiming AMS is that as soon as it is formed it reacts with phenol to form cumylphenol and with itself to form AMS dimer. These products are undesirable and, to the extent phenol reacts with AMS, increase the yield loss in the process. As noted previously, an object of this invention is to minimize the formation of AMS by-products and to maximize the amount of recoverable AMS in the cleavage mixture. The CHP Cleavage Reaction Network is shown in FIG. 1, along with the associated rate constants for the reactions shown.

In most phenol plants, CHP cleavage is run in a continuously-stirred tank reactor (CSTR) by mixing a stream of 82–90% by weight CHP (including the contaminant by-products of oxidation) with a stream of recycle acetone containing the sulfuric acid catalyst. Many producers of phenol by the cumene process conduct the reaction in an excess of acetone ("acetone addition") to raise the AMS yield and to decrease the production of heavies. Such plants typically add acetone in an amount up to 35–40% of the product acetone. However, this excess acetone must be distilled to be recovered, and so various plants will operate at various levels of acetone dilution depending upon the particular economics of their operation in order to maximize AMS production. Accordingly, attempting to improve the AMS yield by varying the acetone dilution is not elegant because of the increased cost of production.

Based on the complexity of the CHP Cleavage Reaction Network and the disparate teachings of the prior art, it is unclear how to maximize the formation of AMS while minimizing its further reaction to waste by-products. As noted in the Background section, the cleavage reaction of CHP is exceedingly rapid. In order to understand the CHP Cleavage Reaction Network, the Network was modelled mathematically only for the reactions with the rate constants $k_1$, $k_4$, and $k_5$. It was later discovered that DCP was a significant component of the mixture under certain conditions, and so $k_2$ and $k_3$ were also examined.

Figure 2A:
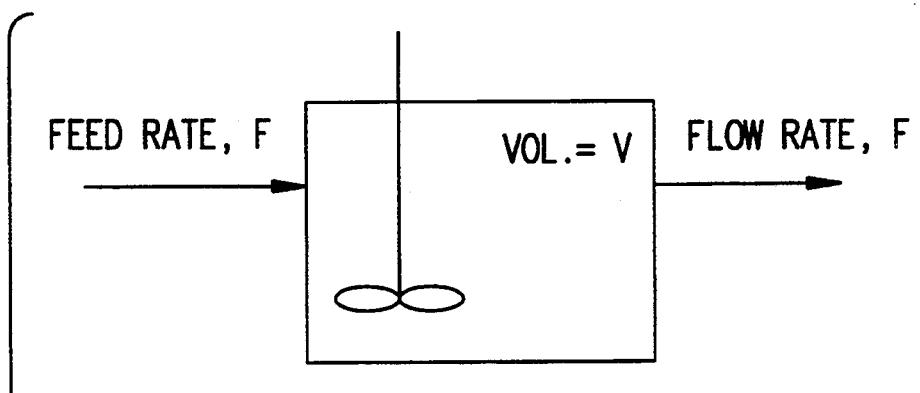

In this kinetic model, the primary reaction of CHP to phenol and acetone was taken as a pseudo first-order reaction as suggested by the literature (Jung and Just, noted above). It was assumed that the dehydration of DMBA and the decomposition of DCP to phenol, acetone, and AMS were also first-order reactions; as shown below, these assumptions were confirmed by data from the batch reactions. The formation of DCP was taken as first order in CHP and first order in DMBA; similarly, the formation of cumylphenol was taken as first order in phenol and first order in AMS. (These modelling assumptions are based on the stoichiometry of the reaction.) Using this modelling technique, the Cleavage Kinetics equations for the Network were derived as shown in FIGS. 2A and 2B. Data from experiments shown below were used to determine the dependence of the rate constants on the variables of temperature and the concentrations of acid, water, and phenol.

Figure 3:
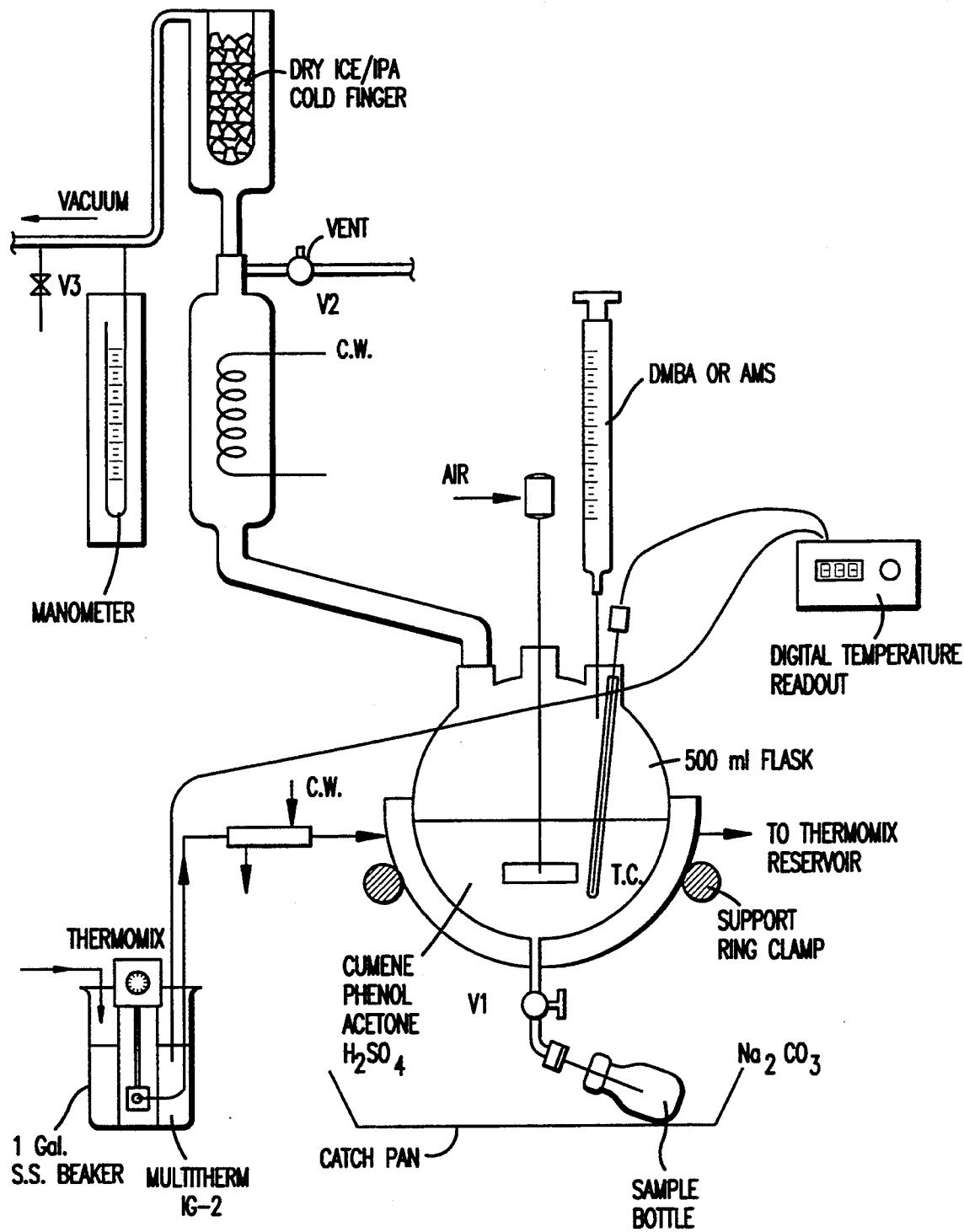
FIG. 3 depicts an experimental apparatus used in the present invention.

Experimentally, $k_3$ and $k_4$ were determined at 60°–80° C. from disappearance rates of DCP and DMBA, respectively, in batch reactions. For reactions run at 60° C., the apparatus is as shown in FIG. 3. This reactor was a 1000-ml., three-necked, round-bottomed, jacketed flask fitted with an agitator, a temperature sensor, a hypodermic for liquid addition, and a bottom valve for sampling the reaction mixture. The system was operated under reflux and the temperature was controlled by varying the pressure (below atmospheric) with a control device. The reactor was filled with a "synthetic cleavate mixture" consisting essentially of phenol, acetone, and cumene, plus a measured amount of sulfuric acid and water, as would essentially comprise the reaction mixture composition typically present in a commercial situation. The typical commercial reactor contains primarily the products phenol and acetone as well as unreacted (unoxidized) cumene and acetophenone, with very minor amounts of acid catalyst and CHP reactant. The reactor was positioned in a jacket through which a hot fluid was circulated to heat the synthetic reaction mixture to reflux. During the reaction period, five or six samples were withdrawn into a 10-ml. serum bottle containing a quench solution (0.5 g. of 10% aqueous sodium carbonate, that was shown to be effective for stopping all of the reactions).

The decomposition of DCP is described by the rate constant $k_3$, and the dehydration of DMBA to AMS and water in the cleavage reactor is described by the rate constant $k_4$. To simulate these reactions in a commercial situation, DCP or DMBA, respectively, was added to the synthetic reaction mixture to initiate the reaction. Experiments were conducted at 60°, 70°, and 80° C. The reaction at 60° C. was conducted with about 200 g. (about 245 ml.) of the synthetic reaction medium. The reactions at 70° and 80° C. were conducted in a reactor equipped and controlled like that shown in FIG. 3, but comprising a one-liter stainless autoclave equiped with an electrical jacket heater; about 400 g. of the synthetic reaction mixture was used. The DCP or DMBA reactant was added from 50–75 ml. charge bombs. Analysis for DCP was performed by high pressure liquid chromatography; analysis of all other components was performed by gas chromatograph.

Figure 4:
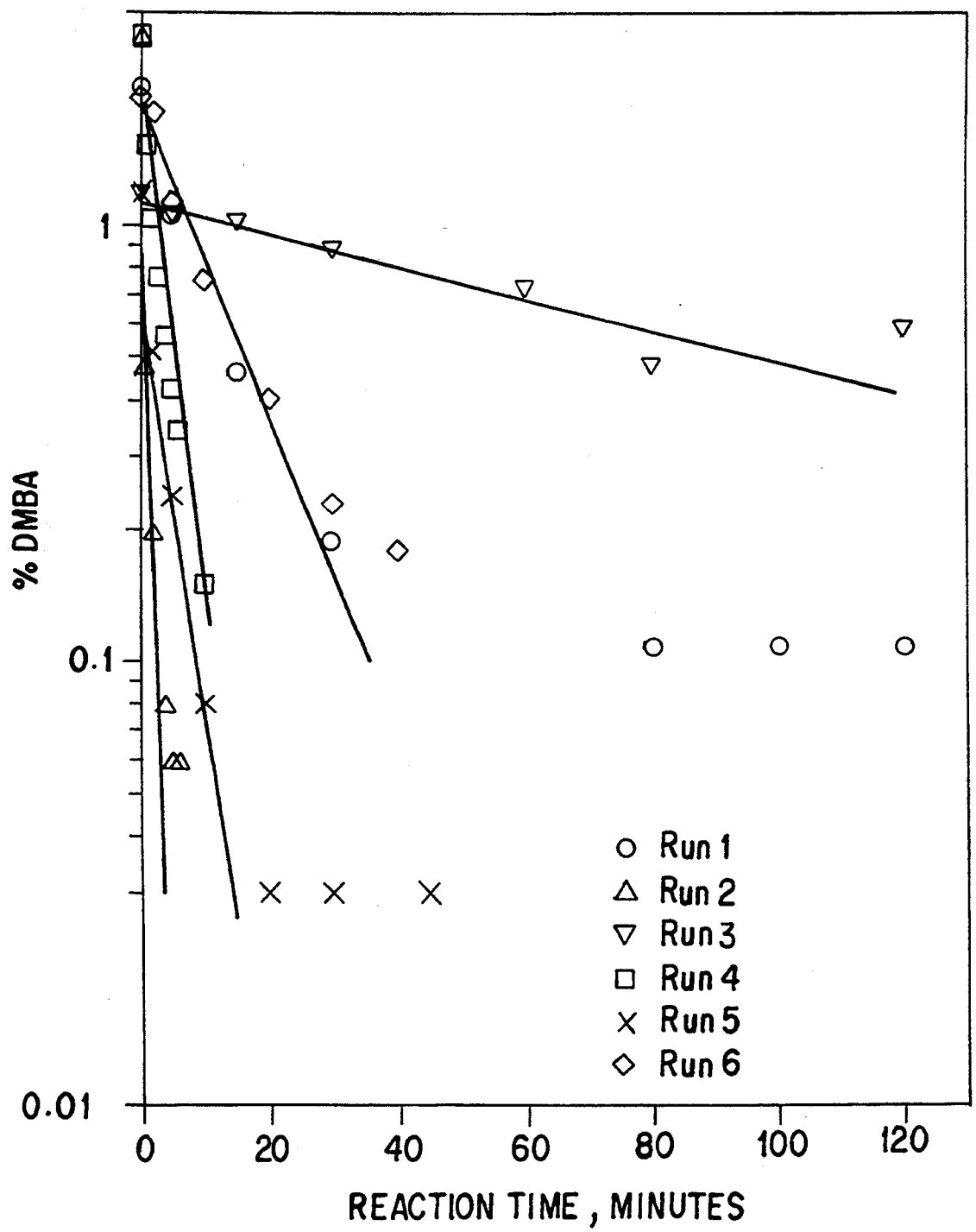
FIGS. 4–5 depict experimental results for the disappearance of DMBA or DCP from a synthetic reaction mixture.
Figure 5:
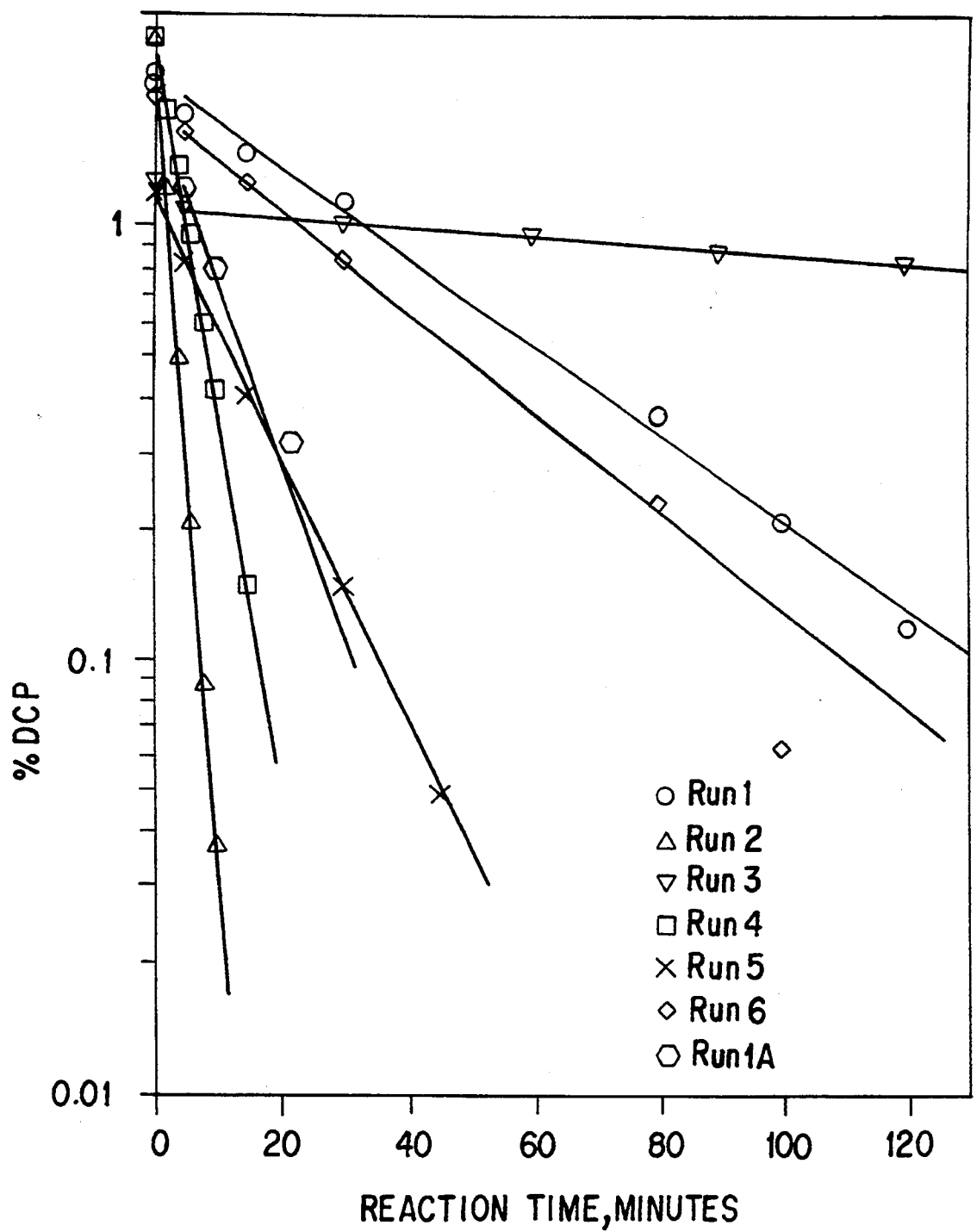

Different amounts of DCP or DMBA were added to the reactor containing known amounts of the various components in the synthetic reaction mixture for six experimental runs. Samples were taken at various times, analyzed, and plotted, such as shown in FIGS. 4 and 5 for the runs performed at 80° C. Slopes from the semi-log plots in the figures were used to determine $k_3$ and $k_4$. The Equations 3.1 and 6.1 were used to derive the same rate constants from the CSTR runs.

These experiments were repeated using a CSTR apparatus similar to that shown in FIG. 3, except that two sets of pumps and dip tubes were provided for the addition of a stream of concentrated CHP in acetone and a stream of acetone containing measured amounts of water and sulfuric acid. These two streams reacted rapidly in the flask thereby generating a reaction mixture consisting essentially of phenol and acetone with minor amounts of cumene, acetophenone, water, and sulfuric acid. Product was removed by an overflow system into a chamber from which samples were withdrawn at desired time intervals.

The primary reaction, the acid-catalyzed decomposition of CHP, is controlled by $k_1$. This reaction is very rapid so the rate constant $k_1$ was calculated from the residual CHP and the residence time in the CSTR. Experiments run in the CSTR mode to simulate the plant reactors gave data that were combined with the batch data to determine the dependence of the rate constants on the reaction variables. A full factorial experimental design (including midpoint replication) was run with the following feed composition (amounts given are percent by weight of the reaction mixture): 0.6% water; 6.3% cumene; 1.3% AP (acetophenone); 5.7% DMBA; and 86.1% CHP. Results of these actual CSTR runs are shown in Table 1 below:

TABLE 1

| Run No. | Temp °F. | Ac* Wt. % | Acid Wt. % | Time min. | Water | CHP | Ac* | Cumene | AMS | Phenol | AP | DMBA | AMS$_2$ | CP | DCP |
|---|---|---|---|---|---|---|---|---|---|---|---|---|---|---|---|
| 1 | 165 | 0 | 0.1 | 5 | 1 36 | 0.016 | 31.59 | 6.40 | 2.86 | 53.80 | 1.51 | 0.71 | 0.69 | 1.04 | 1.10 |
| 2 | 180 | 0 | 0.1 | 5 | 1 50 | 0.017 | 31.03 | 6.29 | 3.04 | 53.24 | 1.35 | 0.44 | 0.91 | 1.13 | — |
| 3 | 165 | 150 | 0.1 | 5 | 1 40 | 0.456 | 56.79 | 4.50 | 1.47 | 36.46 | 1.41 | 1.53 | 0.02 | 0.04 | 0.5 |
| 4 | 180 | 150 | 0.1 | 5 | 1 39 | 0.107 | 55.31 | 4.48 | 2.09 | 37.43 | 1.21 | 0.84 | 0.07 | 0.05 | 1.7 |
| 5 | 165 | 0 | 0.2 | 5 | 1 63 | 0.047 | 31.69 | 6.29 | 2.82 | 52.73 | 1.34 | 0.44 | 0.97 | 1.27 | — |
| 6 | 180 | 0 | 0.2 | 5 | 1 54 | 0.014 | 31.19 | 6.27 | 2.76 | 53.99 | 1.28 | 0.29 | 1.09 | 1.66 | — |
| 7 | 165 | 150 | 0.2 | 5 | 1 37 | 0.173 | 56.68 | 4.46 | 2.21 | 36.64 | 1.26 | 0.73 | 0.08 | 0.07 | 0.6 |
| 8 | 180 | 150 | 0.2 | 5 | 1 37 | 0.041 | 54.61 | 4.46 | 2.68 | 38.20 | 1.11 | 0.56 | 0.13 | 0.11 | — |
| 9 | 165 | 0 | 0.1 | 15 | 1 40 | 0.014 | 31.15 | 6.23 | 2.52 | 53.40 | 1.30 | 0.37 | 1.14 | 1.67 | — |
| 10 | 180 | 0 | 0.1 | 15 | 1 45 | 0.003 | 31.02 | 6.29 | 2.40 | 53.18 | 1.26 | 0.23 | 1.45 | 2.02 | — |
| 11 | 165 | 150 | 0.1 | 15 | 1 47 | 0.077 | 57.51 | 4.46 | 2.28 | 38.08 | 1.14 | 0.82 | 0.10 | 0.01 | 1.1 |
| 12 | 180 | 150 | 0.1 | 15 | 1 72 | 0.037 | 54.18 | 4.42 | 2.71 | 37.23 | 1.00 | 0.50 | 0.16 | 0.13 | — |
| 13 | 165 | 0 | 0.2 | 15 | 1 90 | 0.019 | 31.47 | 6.24 | 2.20 | 51.82 | 1.21 | 0.26 | 1.30 | 1.94 | — |
| 14 | 180 | 0 | 0.2 | 15 | 2 00 | 0.039 | 30.47 | 6.29 | 1.99 | 52.75 | 1.24 | 0.17 | 1.55 | 2.71 | — |
| 15 | 165 | 150 | 0.2 | 15 | 1 69 | 0.002 | 56.25 | 4.44 | 2.72 | 37.30 | 1.04 | 0.50 | 0.17 | 0.15 | — |
| 16 | 180 | 150 | 0.2 | 15 | 1 55 | 0.031 | 54.08 | 4.45 | 2.95 | 38.13 | 0.98 | 0.33 | 0.23 | 0.22 | — |
| 17 | 172.5 | 60 | 0.15 | 10 | 1 52 | 0.021 | 42.42 | 5.36 | 3.08 | 45.59 | 1.15 | 0.40 | 0.45 | 0.55 | — |

TABLE 1-continued

| Run No. | Temp °F. | Ac* Wt. % | Acid Wt. % | Time min. | Water | CHP | Ac* | Cumene | AMS | Phenol | AP | DMBA | AMS$_2$ | CP | DCP |
|---|---|---|---|---|---|---|---|---|---|---|---|---|---|---|---|
| 18 | 172.5 | 60 | 0.15 | 10 | 1 47 | 0.009 | 42.09 | 5.40 | 3.07 | 45.72 | 1.17 | 0.46 | 0.49 | 0.53 | 0.3 |
| 19 | 172.5 | 60 | 0.15 | 10 | 1 54 | 0.020 | 42.92 | 5.40 | 3.10 | 45.43 | 1.17 | 0.46 | 0.47 | 0.48 | — |
| 20 | 179 | 38 | 0.19 | 12 | 1 25 | 0.075 | 38.86 | 5.70 | 2.72 | 48.52 | 1.14 | 0.15 | 1.03 | 1.37 | — |
| 21 | 174 | 38 | 0.19 | 12 | 1 42 | 0.029 | 37.99 | 7.72 | 3.00 | 47.37 | 1.16 | 0.31 | 0.77 | 0.97 | — |

*Ac = acetone

From these rate constants component yields were calculated for simulated runs using various reaction conditions at various residence times; these results are shown in Table 2. More particularly, this Table 2 shows the calculated yields for residence times of ten minutes, and the calculated residence times for maximum AMS yield. The calculations were done by using the rate equations in a static, iterative material balance computer simulation to derive the component concentrations.

The design of the experiments run in both the batch and continuous modes was contrived with special attention to the factors believed to have some influence on the phenol production process. For example, increasing the reaction temperature or the acid concentration increased the rates of all of the reactions, whereas minor addition of water caused a decrease in the rates. However, significant addition of acetone, while decreasing all of the rates (because of the catalytic effect of phenol), also caused a significant decrease in the rate of formation of heavies (AMS dimer and cumylphenol) relative to the rate of AMS formation. Thus, there is presented the problem of determining whether some parameter or combination of conditions could lead to higher yields of AMS.

Results shown in Table 2 for these simulated runs employed the rate constants determined experimentally and a standard acetone addition of 38%. The Table shows some results unexpected from the typical plant operating philosophy. For example, the maximum yield of AMS from DMBA occurs at higher temperatures and at higher acid concentrations. More unusually, maximum AMS yields occured at shorter residence times (e.g., Run Nos. 16 and 17, with 1.6 and 1.8 minute respective residence times), which is contrary to the prevailing wisdom in the industry. The conventional philosophy is that the best AMS yield is obtained under mild conditions, a conclusion formed at actual plants from operating results at residence times of ten minutes or longer. The results shown in Table 2 indicate that the maximum yield of AMS from DMBA dehydration occurs in a very short period of time. These results suggest an AMS yield of 83% at a residence time of only 1.6 min. (96 sec.) for the conditions of the fourth run at 80° C.

TABLE 2

| | | | | Residence Time = 10 min. | | | | Maximum AMS Yield | | | |
|---|---|---|---|---|---|---|---|---|---|---|---|
| Run No. | Temp °F. | Acid (wt. %) | Recycle | Water (wt. %) | AMS Molar Yield from DMBA | DMBA | DCP | Time (min.) | AMS Molar Yield from DMBA | DMBA | DCP |
| 1 | 165 | 0.1 | 38 | 0.77 | 0.63 | 0.06 | 0.016 | 4.2 | 0.71 | 0.11 | 0.053 |
| 2 | 165 | 0.1 | 38 | 0.96 | 0.64 | 0.08 | 0.031 | 5.8 | 0.68 | 0.12 | 0.063 |
| 3 | 165 | 0.1 | 38 | 1.44 | 0.61 | 0.14 | 0.086 | 10.0 | 0.61 | 0.14 | 0.084 |
| 4 | 165 | 0.2 | 38 | 0.79 | 0.59 | 0.02 | 0.005 | 2.4 | 0.78 | 0.08 | 0.044 |
| 5 | 165 | 0.2 | 38 | 0.99 | 0.63 | 0.04 | 0.010 | 3.4 | 0.76 | 0.08 | 0.050 |
| 6 | 165 | 0.2 | 38 | 1.47 | 0.67 | 0.07 | 0.033 | 6.0 | 0.70 | 0.10 | 0.067 |
| 7 | 172.5 | 0.1 | 38 | 0.78 | 0.60 | 0.04 | 0.008 | 3.0 | 0.74 | 0.10 | 0.048 |
| 8 | 172.5 | 0.1 | 38 | 0.97 | 0.63 | 0.06 | 0.016 | 4.2 | 0.71 | 0.11 | 0.056 |
| 9 | 172.5 | 0.1 | 38 | 1.46 | 0.64 | 0.11 | 0.051 | 7.6 | 0.65 | 0.13 | 0.072 |
| 10 | 172.5 | 0.2 | 38 | 0.79 | 0.54 | 0.02 | 0.002 | 1.8 | 0.81 | 0.07 | 0.037 |
| 11 | 172.5 | 0.2 | 38 | 1.00 | 0.60 | 0.02 | 0.005 | 2.6 | 0.79 | 0.07 | 0.041 |
| 12 | 172.5 | 0.2 | 38 | 1.50 | 0.66 | 0.05 | 0.017 | 4.4 | 0.74 | 0.09 | 0.058 |
| 13 | 180 | 0.1 | 38 | 0.78 | 0.56 | 0.03 | 0.004 | 2.4 | 0.77 | 0.09 | 0.038 |
| 14 | 180 | 0.1 | 38 | 0.99 | 0.61 | 0.04 | 0.009 | 3.2 | 0.74 | 0.10 | 0.047 |
| 15 | 180 | 0.1 | 38 | 1.48 | 0.65 | 0.08 | 0.028 | 5.6 | 0.69 | 0.12 | 0.063 |
| 16 | 180 | 0.2 | 38 | 0.80 | 0.49 | 0.01 | 0.001 | 1.6 | 0.83 | 0.06 | 0.030 |
| 17 | 180 | 0.2 | 38 | 1.00 | 0.55 | 0.02 | 0.002 | 1.8 | 0.81 | 0.07 | 0.038 |
| 18 | 180 | 0.2 | 38 | 1.51 | 0.63 | 0.03 | 0.008 | 3.4 | 0.76 | 0.08 | 0.047 |
| 19 | 172.5 | 0.1 | 38 | 0.78 | 0.60 | 0.04 | 0.008 | 3.0 | 0.74 | 0.10 | 0.048 |
| 20 | 172.5 | 0.1 | 0 | 0.86 | 0.43 | 0.03 | 0.005 | 2.0 | 0.70 | 0.11 | 0.058 |
| 21 | 172.5 | 0.1 | 60 | 0.74 | 0.66 | 0.04 | 0.010 | 3.8 | 0.76 | 0.09 | 0.040 |

Figure 6:
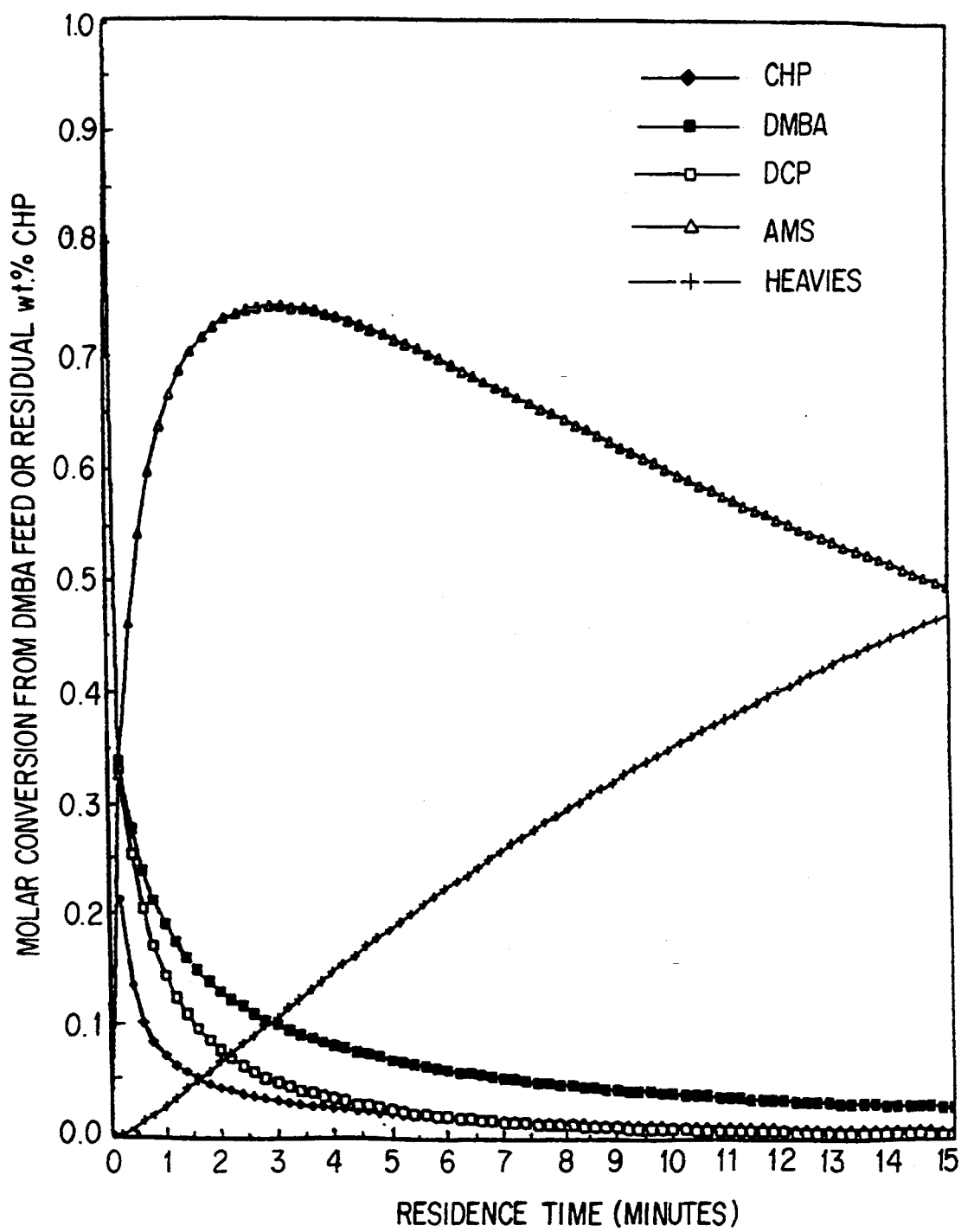
FIGS. 6–9 depict simulated results of certain reaction products from a CSTR reactor operated under different conditions; namely, under typical plant conditions (FIG. 6), under relatively milder (FIG. 7) and more stringent (FIG. 8) conditions, and results of the effects of temperature at lower residence times (FIG. 9).
Figure 7:
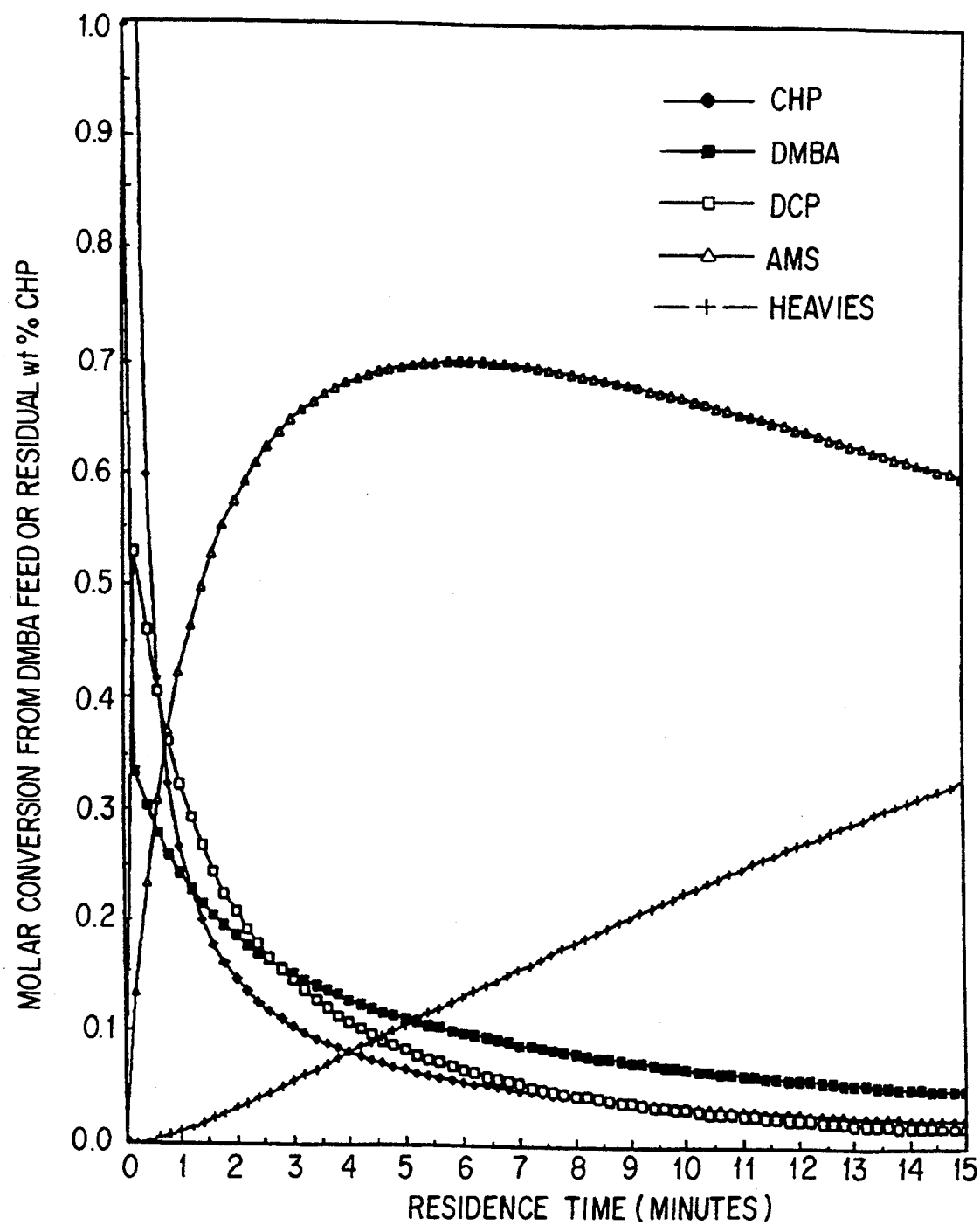
Figure 8:
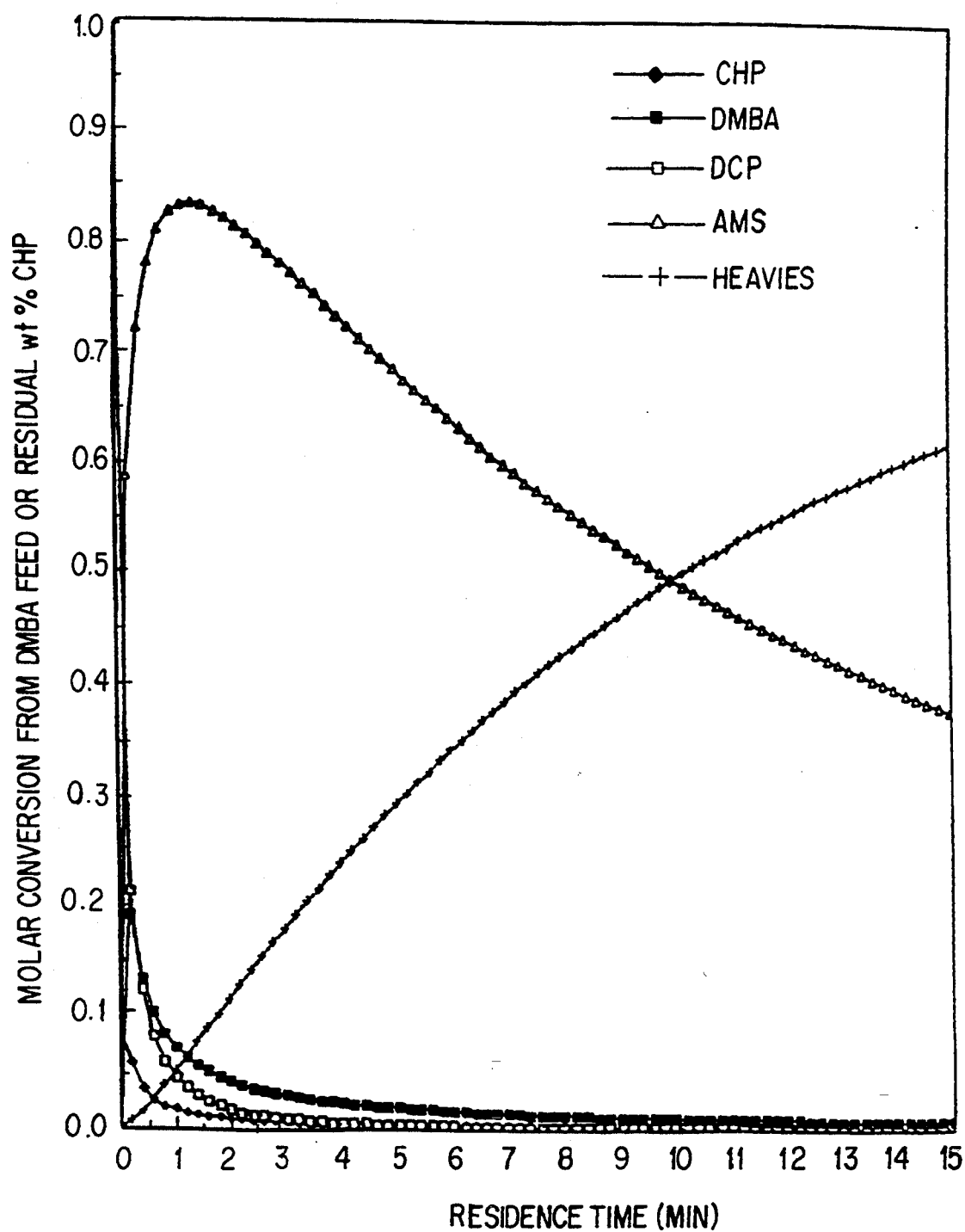
Figure 9:
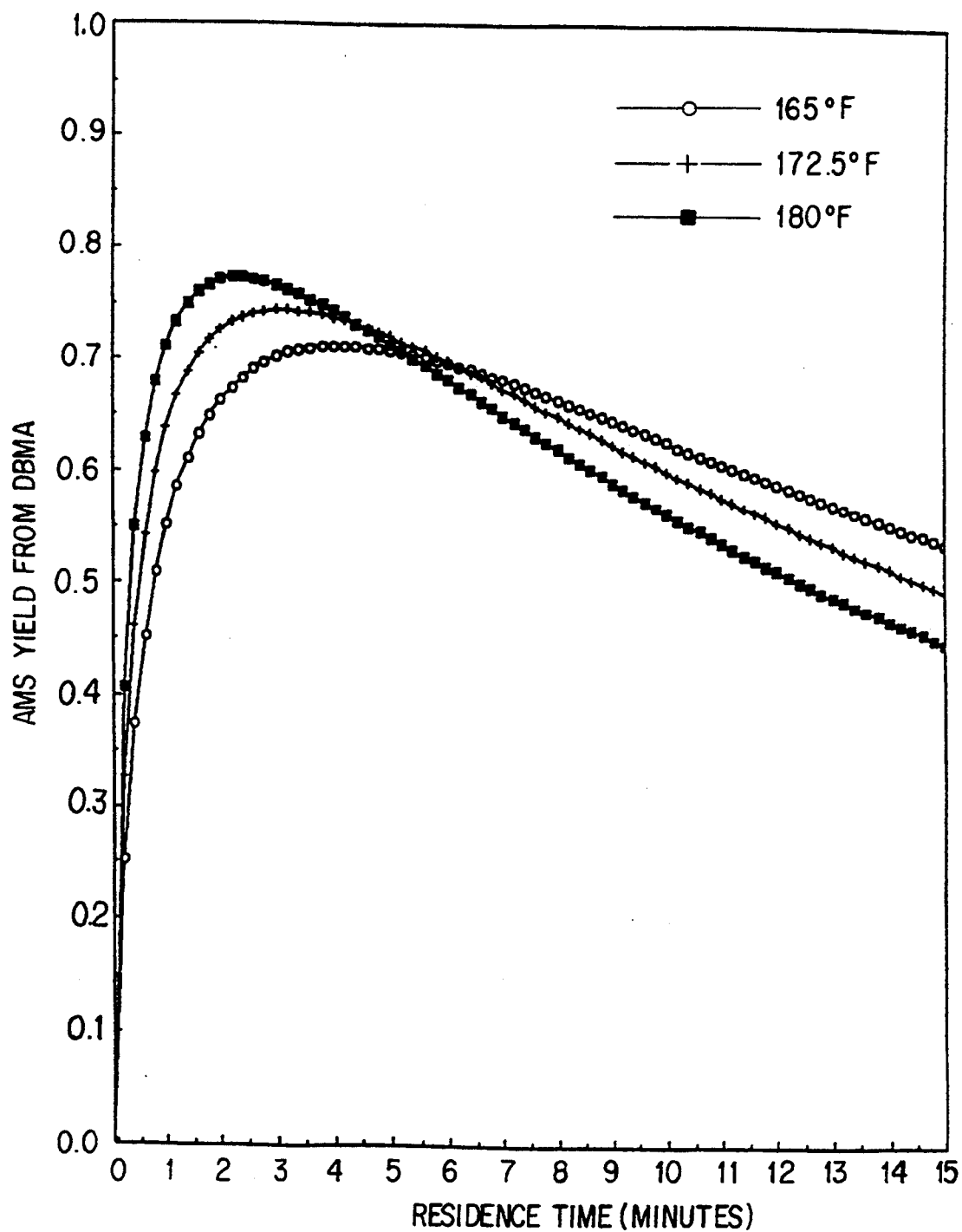

All of these results tend to show that the maximum AMS yield occurs rather rapidly, generaly within five minutes of reaction. In practice, plants typically use residence times of ten to twenty minutes. Therefore, it is apparent from my work that the typical plant residence time is a poor choice and has overshot the most desirable region for AMS yield. FIG. 6, based on typical operating conditions, shows that the higher yield of AMS at shorter residence times is accompanied by an increase in the residual concentrations of CHP, DMBA, and DCP, which are undesirable with respect to the yield of both phenol and recoverable by-products. The presence of residual compounds is higher at lower temperatures (FIG. 7) and lower at higher temperatures (FIG. 8). These simulated results show that a variety of conditions, especially low residence times, will improve the AMS yield. These simulations also show that the most desirable conditions for driving the phenol-producing reaction, high acid concentration, low water concentration, and higher temperatures, will also suppress undesired residual products. FIG. 9 shows that while lower temperatures would give better AMS yields at a typical plant residence time of 10 to 15 minutes, higher temperatures give even better AMS yields at residence times of not more than about four minutes. More preferably, residence times of not more than about three minutes, and most preferably not more than about one minute, are used in the invention, with about 30 sec. being the minimum desirable residence time.

Of course, it is seen from the entirety of the experimental and simulated results that the optimum conditions will be affected most significantly by temperature, sulfuric acid concentration, water concentration, and acetone addition. For example, from FIG. 9, it is seen that at 180° F. the minimum desirable residence time is about 30 seconds, while at 172.5° F. the time increase to about one minute, and at 165° F. the minimum is about 1.5 minutes. Thus, given the typical plant conditions on which FIG. 9 is based, at 180° F. residence times less than ten minutes and greater than one-half minute provide improved yields. Thus, the present invention provides a method for improving the AMS yield by decreasing the residence time of the reaction while enabling the artisan to determine the improved operating window. In the present invention, the cleavage reaction is conducted at 50°-90° C., more preferably at 60°-85° C., and most preferably at 70°-80° C.

It is also interesting to note the effect of acetone addition on the reaction scheme. The effect of addition on AMS yield is likely to be much greater at the ten minute residence times commonly used in plants, than at the shorter residence times according to the present process. Note, for example, the standard acetone additions of 38% used for the runs shown in Table 2. Also note that the maximum AMS yield at the ten minute residence time is 0.67, and 0.66 at 60% acetone addition. In contrast, the maximum AMS yield, even at no acetone addition, is greater at residence times of generally 10%-40% of the residence times typically used in plants. Therefore, by practicing this invention, with or without acetone addition, the artisan can decrease the residence time significantly from that typically used in plants and raise AMS yields by amounts not attainable at the typical plant residence time. Nevertheless, in view of this invention, the artisan may envision various combinations of reduced residence time and acetone addition to decrease the effective residence time and thus still obtain the benefits of the present invention.

Figure 10:
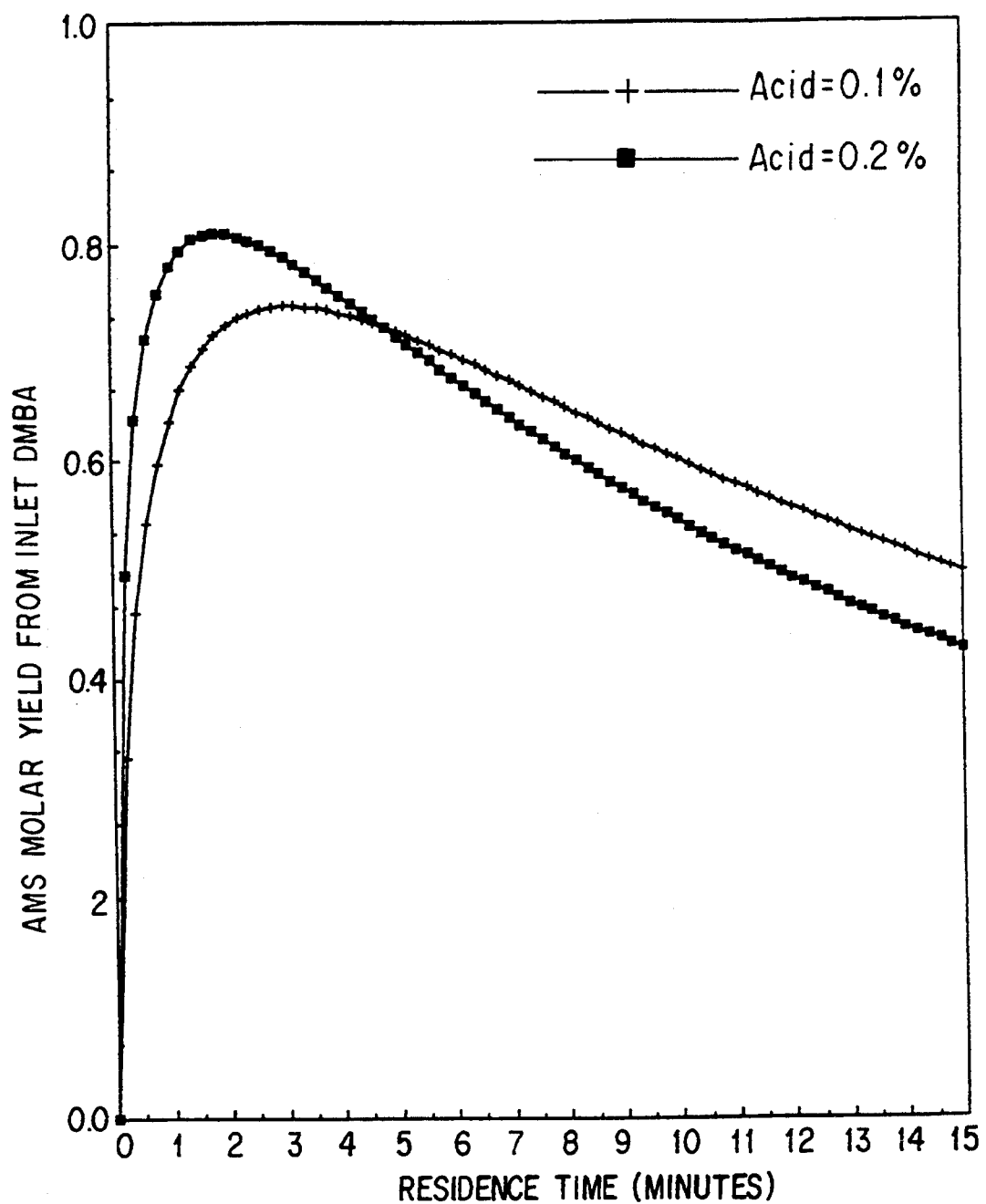
FIGS. 10–11 depict simulated results of AMS yield from DMBA using the base conditions used in FIG. 6 while varying the acid content of the reaction mixture (FIG. 10) and the acetone recycle (FIG. 11).
Figure 11:
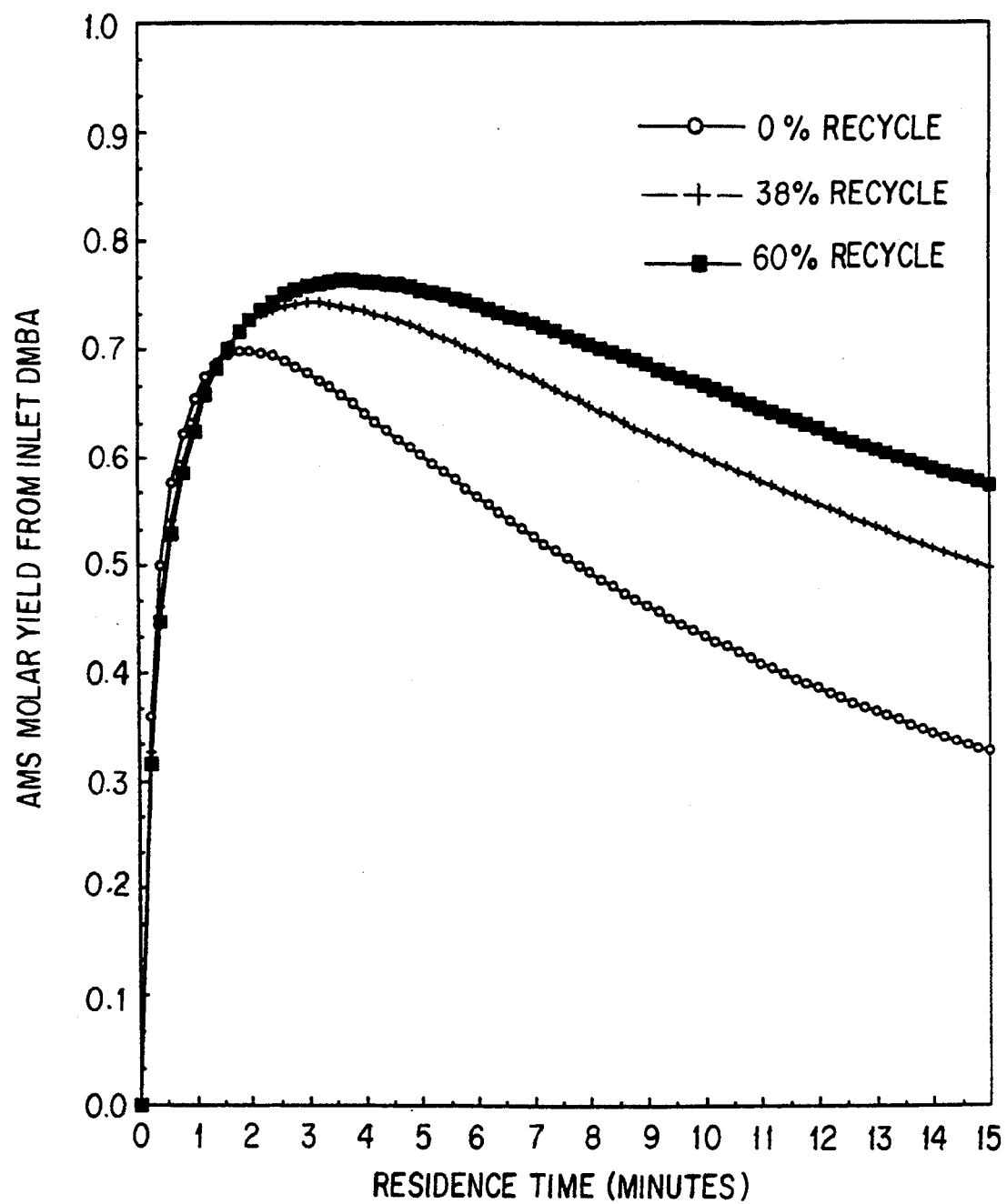
Figure 12A:
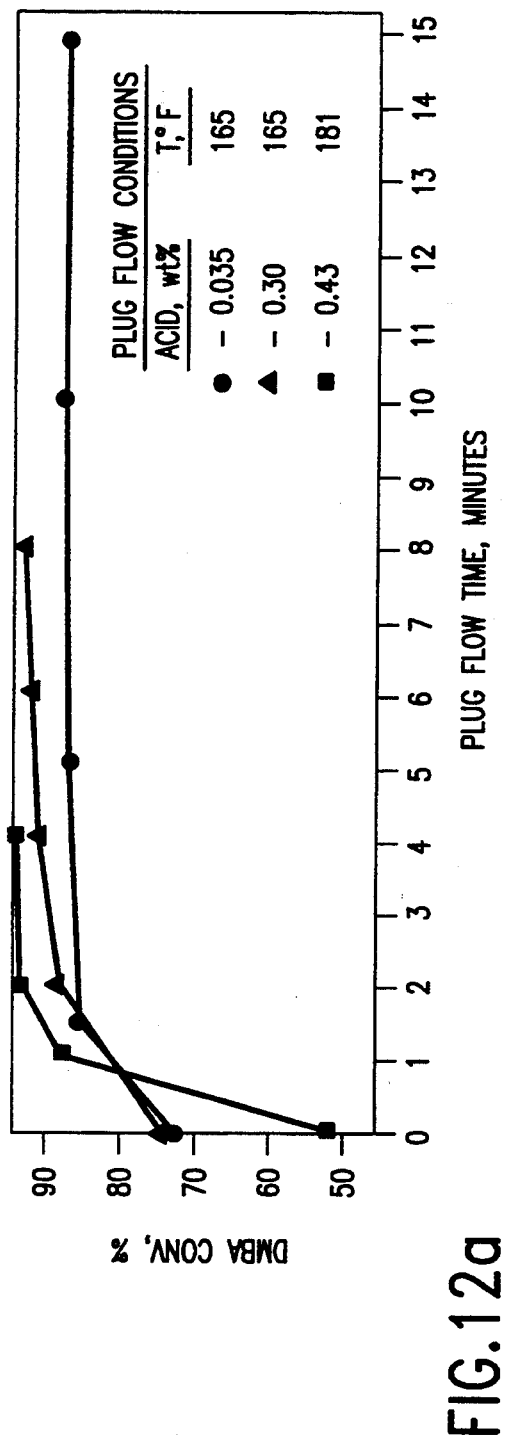
FIG. 12 depicts experimental results on the compositions of products from a series combination of a CSTR and a PFR (solid lines) simulated by batch reaction, each operated at a four-minute residence time, compared with a CSTR operated at an eight minute residence time.
Figure 12B:
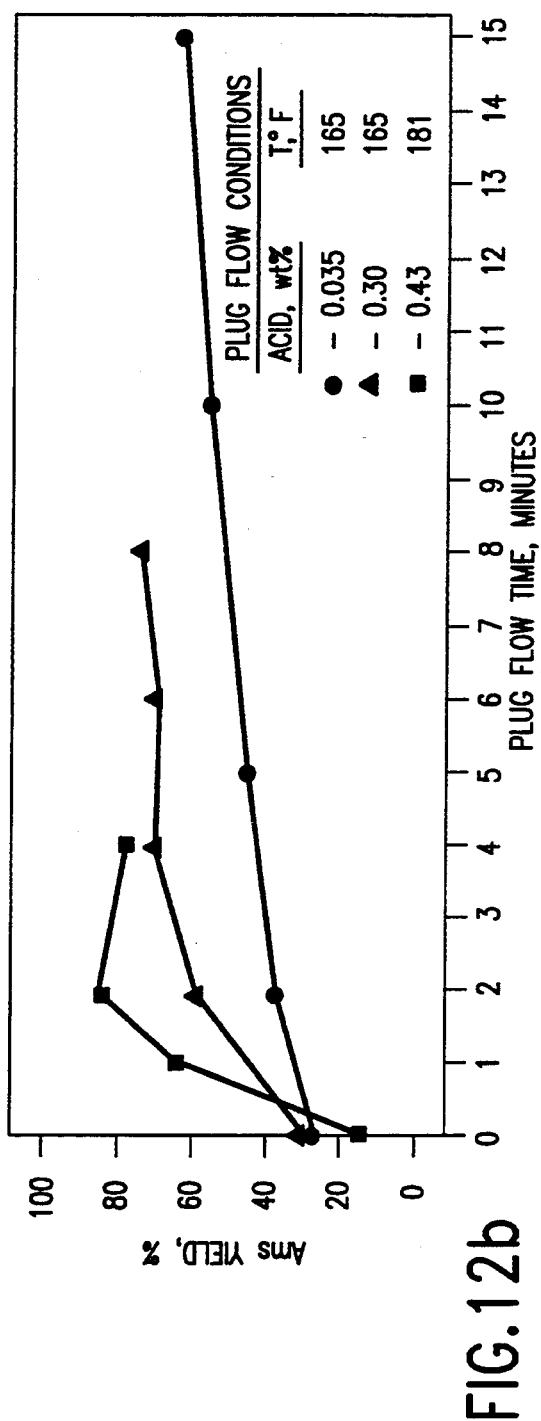
Figure 12C:
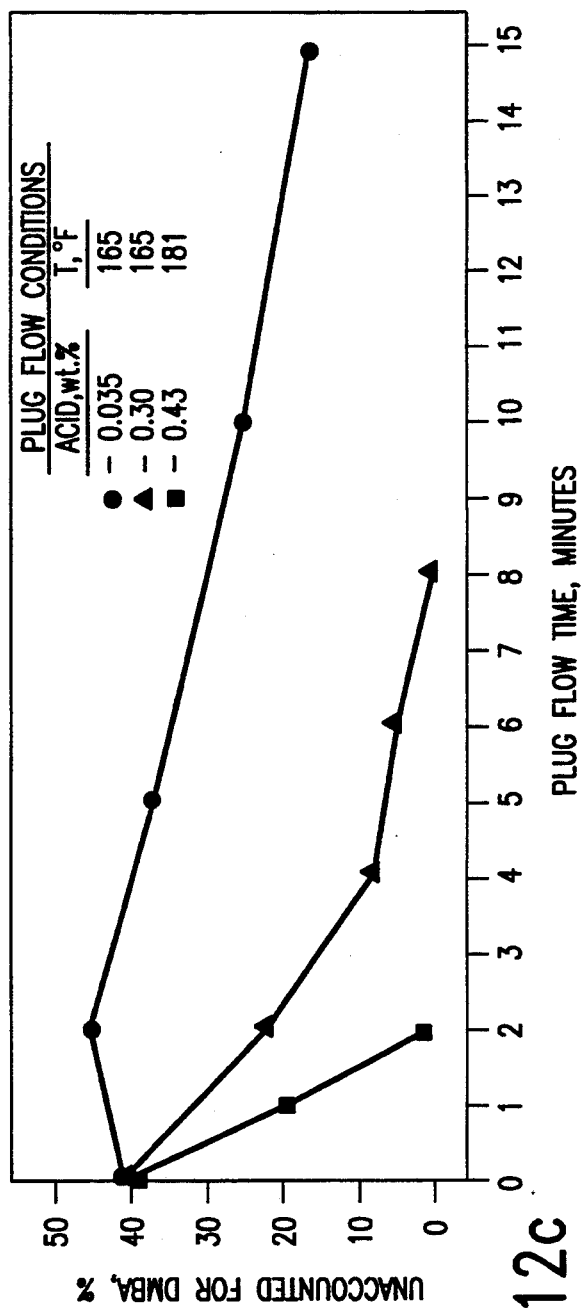
Figure 12D:
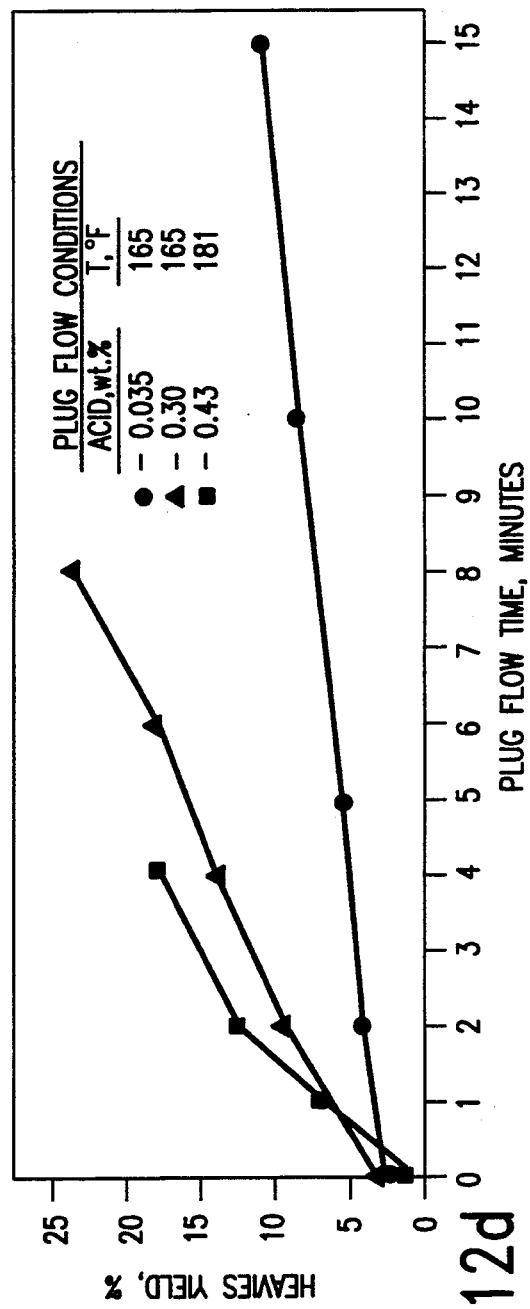

The kinetic model indicating that reduced residence times are beneficial for increasing AMS yield without the formation of heavies was further verified by using the conditions on which FIG. 6 is based (typical plant feed of 0.6% water, 6.3% cumene, 1.3% AP, 5.7% DMBA, and 86.1% CHP) at a reaction temperature of 172.5° F. and a theoretical exit water concentration of 0.8%. In these runs, the single parameters of acid concentration and acetone addition were varied. As shown in FIG. 10, using an acetone addition of 38%, the highest yield of AMS based on the inlet DMBA concentration occurs at about 2 minutes with an acid concentration of 0.1%. Increasing the acid concentration to 0.2% not only increases the molar yield of AMS as shown in the figure, but the residence time is further reduced to about one minute. According to the present invention, the cleavage reaction is preferably conducted with an acid concentration of 0.075-0.3 wt. %, and most preferably at 0.1-0.25 wt. %, although lesser and greater amounts of acid are disclosed in the literature. FIG. 11 shows that increasing the acetone addition (recycle) also increases AMS yield, but tends to increase the residence times slightly. Nevertheless, it is still seen in FIG. 11 that better yields of AMS occur at shorter residence times. It is interesting to note in FIG. 11 that at typical plant residence times of 10 minutes, the addition of acetone significantly increases the AMS yield, yet even at no acetone addition decreased residence times provide an even higher yield. It can also be noted that at 60% acetone addition there is less of an increase in AMS yield at a typical 10 minute residence time, and still the AMS yield is not as great as can be achieved with no acetone addition at significantly reduced residence times.

A single CSTR reactor is the typical reactor configuration for commercial phenol plants. In the present invention, another embodiment is a series combination of reactors including at least one CSTR, and optionally including at least one plug-flow reactor (PFR). The PFR may simply be comprised of a pipe adapted with means for removing the heat of reaction; exemplary heat exchange devices include fins or a heat exchange fluid circulated in a jacket around the pipe. In a single CSTR-PFR system, the main reaction of CHP to yield phenol and acetone occurs in the CSTR, as is preferrable because of the ample ability to remove the heat of reaction by refluxing acetone. The subsequent diminution of residuals, the dehydration of DMBA to AMS with reduced formation of AMS dimer and cumylphenol, occurs mainly in the PFR, where the reaction is only slightly exothermic. However, the high enthalpy of the CHP cleavage reaction (55 kcal/g.mole) will likely require a heat exchange means to remove heat from the PFR.

The advantage of using a PFR derives from the lower residence time than that required for a CSTR for a desired degree of reaction of DMBA. In effect, the AMS has less time to be converted to heavies. From a theoretical point of view, it would be beneficial to conduct the entire reaction in a PFR-type vessel because of the lower residence times required. On the other hand, the practical difficulties in removing heat sufficiently rapidly from a PFR strongly suggest the use of a CSTR. Therefore, it is preferred to operate with the majority of the reaction occuring in a PFR to the extent constrained by heat removal and other safety parameters. Thus, it is preferred in any combination of CSTRs and PFRs to use a CSTR as the first in the series. Because a series of n CSTRs in series approaches PFR kinetics as n increases, another preferred embodiment is a series of CSTR reactors having a reduced total residence time. In essence, the typical mode of production using a single CSTR operated at a longer residence time appears to have been virtually a worst case choice for kinetics.

A CSTR-PFR sequence was simulated in the laboratory by running a CSTR until steady state concentrations were reached. The flows into and out from the CSTR were then stopped and the reactor was run in a batch mode. The composition of the batch reaction was noted over a period of time. Samples taken during the batch mode operation are considered equivalent to those that could have been taken at different locations along the length of a PFR having a constant volumetric flow rate; the elapsed time in the batch mode thus corresponds to the distance (and extent of reaction) along the axial length of a PFR.

TABLE 3

| CSTR and PFR in Series | | | | | |
|---|---|---|---|---|---|
| FIRST STAGE CSTR | | | SECOND STAGE PFR | | |
| Time* | AMS/ DMBA$_0$ | DMBA/ DMBA$_0$ | Time* | AMS/ DMBA$_0$ | DMBA/ DMBA$_0$ |
| 25 | 0.3638 | 0.6305 | 115 | 0.8522 | 0.0434 |
| 75 | 0.6020 | 0.3626 | 90 | 0.8304 | 0.478 |

TABLE 3-continued

| CSTR and PFR in Series | | | | | |
|---|---|---|---|---|---|
| FIRST STAGE CSTR | | | SECOND STAGE PFR | | |
| Time* | AMS/ DMBA$_0$ | DMBA/ DMBA$_0$ | Time* | AMS/ DMBA$_0$ | DMBA/ DMBA$_0$ |
| 125 | 0.6753 | 0.2544 | 65 | 0.8087 | 0.565 |
| 225 | 0.7053 | 0.1594 | | | |
| 1100 | 0.5316 | 0.0373 | | | |

*Time in seconds for maximum AMS/DMBA$_0$ (i.e., maximum AMS yield). It shoud be noted tat "AMS yield" as generally used herein denotes the amount of AMS formed based on the amount of DMBA charged to the reactor, rather than based on the amount of total reactant consumed. Thus, AMS yield as shown in Table 3 can be considered the selectivity or ultimate yield of AMS based on the theoretical amount of DMBA which could have been converted.

The results shown in Table 3 are for simulated runs using a series combination of a CSTR and a PFR, both at 172.5° F. These runs were based on a reaction mixture calculated as derived from two feeds, one providing 72% CHP, 2.5% DMBA, 0.5% AP (acetophenone), and 12.9% cumene, and the other providing 11.2% acetone, 0.12% sulfuric acid, and 0.8% water (total reaction mixture weight basis). The CSTR stages were run at simulated residence times of 25, 75, and 125 seconds. The ultimate yield of AMS ("AMS/DMBA$_0$") and the residual fractional DMBA remaining ("DMBA/DMBA$_0$") are shown in the left hand portion of Table 3 for the CSTR portion of the simulation. On the right hand side are the resulting fractional yield of AMS and residual DMBA by reacting the simulated effluent from each CSTR in a PFR for the residence times shown. The CSTR-only simulations for a 225 sec. residence time and a 1110 sec. residence time (18.5 min.; typical for some commercial plants), are shown for comparison. As seen, operating a CSTR alone at a reduced residence time of about 3½ min. provides significant improvements over longer CSTR residence times.

As also seen from Table 3, extended plant runs of these types would be expected to yield only about 50% conversion of DMBA to AMS (although numerical values may likely be lower for actual plants because the formation of DCP was not considered in modelling the simulation used to derive Table 3), whereas the CSTR-PFR combination of this invention consistently provides conversion levels (ultimate yields) of at least 80%. Conventional plant designs do not include any operation for recovering unconverted DMBA from the product stream. Accordingly, it is desirable to drive the DMBA dehydration to completion to form AMS (without an increased formation of heavies), since any unreacted DMBA is removed and lost via the heavy ends stream. The improved conversion to AMS without the increased formation of heavies provided by this invention thus solves another typical production problem.

A comparison of CSTR and combined CSTR-PFR reaction systems is displayed in FIG. 12, with PFR feed taken from the CSTR contents after a four-minute residence time. The horizontal dotted line represents the composition of a CSTR at steady state with a residence time of eight minutes, and the solid lines represent the results of using first a CSTR with a four-minute residence time followed by a PFR with a four-minute residence time; effectively, the same residence time with a different reactor arrangement, thus allowing for PFR kinetics to effect the process. Although a single CSTR provides good AMS yields initially, it can be seen that the combined system provides an improved AMS yield after about a 2½-minute residence time in the PFR, and the production of heavies is at all times lower than in the CSTR. In the practice of a single CSTR-PFR system, the novel residence time for each reactor would be as given above for the single CSTR system, 0.5–5 min., preferably below about three minutes, and most preferably below about one minute, depending upon such process conditions as acid concentration and acetone addition.

A further examination of the CSTR data shown in Table 3 suggests one problem a plant has in reducing the residence time from 1100 to 225 seconds is that unconverted DMBA goes up from 3.7% to about 16% in the simulation (with actual amounts being lower as mentioned above). A further reduction in residence times leaves even more unconverted DMBA which exits in the heavies stream but which would increase the steady state concentration. However, when a second stage (a PFR in this example, although another CSTR could be used) is provided for reaction, the DMBA conversion can be raised and high yields of AMS can be obtained. The PFR times shown in Table 3 were selected for maximum AMS yields and were based on simulated runs using the respective CSTR effluent compositions.

The foregoing experimental and predictive results are meant to explain and describe the invention, and are not intended to limit the invention to only those parameters specifically disclosed. Thus, upon perusing this specification, various modifications of the foregoing description may become apparent, and such are intended to be within the scope and spirit of the invention as defined by the following claims.

What is claimed is:

1. An improved process for the production of phenol or a derivative thereof by the acid-catalyzed cleavage of a feedstock comprising a reactant cumene hydroperoxide and a contaminant by-product dimethylbenzyl alcohol to convert the hydroperoxide to phenol (or said derivative thereof) and α-methyl styrene, wherein the improvement comprises conducting the cleavage reaction in at least one stirred reactor during a residence time of not more than about five minutes effective to promote reaction of the dimethylbenzyl alcohol to α-methyl styrene wherein a product effluent is fed from said stirred reactor to a plug-flow reactor for additional conversion of the dimethylbenzyl alcohol to α-methyl styrene.

2. The process as defined by claim 1, wherein the residence time in the plug-flow reactor is not more than about five minutes.

3. The process as defined by claim 2, wherein the residence time in the plug-flow reactor is not more than about three minutes.

4. The process defined by claim 3, wherein the residence time is not more than about one minute.

5. The process as defined by claim 1, wherein the residence time in the plug-flow reactor is not more than about three minutes.

6. The process as defined by claim 5, wherein the residence time in the stirred reactor is not more than about one minute.

7. The process as defined by claim 1, further comprising diluting said feedstock with an inert diluent prior to cleaving the aralkyl hydroperoxide.

8. The process as defined by claim 1, further comprising adding to said feedstock 0–60% by weight of an inert diluent.

9. The process as defined by claim 8, which comprises adding 35–40 wt. % of an inert diluent.

10. The process as defined by claim 9, wherein the inert diluent consists essentially of acetone.

11. The process as defined by claim 1, wherein the cleavage reaction is conducted at a temperature in the range of approximately 50°–90° C.

12. The process as defined by claim 11, wherein the temperature is in the range of approximately 70°–80° C.

13. The process as defined by claim 1, wherein the acid catalyst is present in an amount of approximately 0.075–0.3 wt. %.

14. The process as defined by claim 13, wherein the acid catalyst is present in an amount of approximately 0.1–0.25 wt. %.

15. An improved process for the production of phenol or a derivative thereof by the acid-catalyzed cleavage of a feedstock comprising a reactant cumene hydroperoxide and a contaminant by-product dimethylbenzyl alcohol to convert the hydroperoxide to phenol (or said derivative thereof) and $\alpha$-methyl styrene, wherein the improvement comprises conducting the cleavage reaction in at least one stirred reactor during a residence time of not more than about five minutes effective to promote reaction of the dimethylbenzyl alcohol to $\alpha$-methyl styrene and further comprising feeding a product effluent from said stirred reactor to a second stirred reactor for additional conversion of the dimethyl benzyl alcohol to $\alpha$-methyl styrene, the total residence time not being more than about five minutes.

16. The process as defined by claim 15, wherein the total residence time is not more than about three minutes.

17. The process as defined by claim 16, wherein the total residence time is not more than about one minute.

* * * * *